United States Patent [19]
Helland et al.

[11] Patent Number: 5,318,572
[45] Date of Patent: Jun. 7, 1994

[54] HIGH EFFICIENCY TISSUE STIMULATING AND SIGNAL SENSING ELECTRODE

[75] Inventors: John R. Helland, Santa Clarita; Diane M. Muff, Granada Hills, both of Calif.

[73] Assignee: Siemens Pacesetter, Inc., Sylmar, Calif.

[21] Appl. No.: 892,463

[22] Filed: Jun. 2, 1992

[51] Int. Cl.⁵ ............................................. A61N 1/05
[52] U.S. Cl. .................................... 607/121; 607/122
[58] Field of Search ................ 128/784, 785, 786, 642

[56] References Cited

U.S. PATENT DOCUMENTS

| | | | |
|---|---|---|---|
| B1 3,911,928 | 11/1988 | Lagergren | 128/786 |
| 3,911,928 | 10/1975 | Lagergren | 128/419 |
| 4,033,357 | 7/1977 | Helland et al. | 128/419 |
| 4,101,984 | 7/1978 | MacGregor | 128/419 P |
| 4,280,514 | 7/1981 | MacGregor | 128/786 |
| 4,281,668 | 8/1981 | Richter et al. | 128/784 |
| 4,281,669 | 8/1981 | MacGregor | 128/784 |
| 4,408,604 | 10/1983 | Hirshorn et al. | 128/785 |
| 4,444,206 | 4/1984 | Gold | 128/784 |
| 4,502,492 | 3/1985 | Bornzin | 128/785 |
| 4,534,366 | 8/1985 | Soukup | 128/786 |
| 4,542,752 | 9/1985 | DeHaan et al. | 128/784 |
| 4,603,704 | 8/1986 | Mund et al. | 128/784 |
| 4,606,118 | 8/1986 | Cannon et al. | 29/825 |
| 4,649,937 | 3/1987 | DeHaan et al. | 128/784 |
| 4,679,572 | 7/1987 | Baker, Jr. | 128/786 |
| 4,711,251 | 12/1987 | Stokes | 128/784 |
| 4,844,099 | 7/1989 | Skalsky et al. | 128/785 |
| 4,934,381 | 6/1990 | MacGregor | 128/784 |
| 4,936,317 | 6/1990 | MacGregor | 128/784 |
| 4,945,922 | 8/1990 | van Krieken | 128/785 |

OTHER PUBLICATIONS

Timmis, G. C., M.D. et al., "The Evolution of Low Threshold Leads," *Clin. Prog. in Pacing and Electrophysiol.*, vol. 1, No. 4, 1983, pp. 313-334.

Mond, H. G., "Development of Low-Stimulation-Threshold, Low-Polarization Electrodes," *New Perspectives in Cardiac Pacing 2*, Chapter 7, pp. 133-162 (Futura Publishing Company, Inc., Mt. Kisco, N.Y.-1991).

*Primary Examiner*—William E. Kamm
*Assistant Examiner*—Scott M. Getzow
*Attorney, Agent, or Firm*—Leslie S. Miller; Samuel M. Katz

[57] ABSTRACT

A pacing lead having a porous electrode of platinum-iridium with recessed areas or grooves formed into the surface. The grooves allow for acute electrode stabilization as a result of clot formation and endocardial tissue capture during insertion and immediate immobilization upon implant. At least one layer of a porous coating of 20-200 micron diameter spherical particles are deposited on the surface of the base electrode to obtain a porous macrostructure for promoting chronic tissue ingrowth. Additionally, a microstructure surface coating is applied to increase the active surface area and enhance electrical efficiency by lowering electrochemical polarization and increasing electrical capacitance.

24 Claims, 4 Drawing Sheets

HIGH EFFICIENCY TISSUE STIMULATING AND SIGNAL SENSING ELECTRODE

BACKGROUND OF THE INVENTION

This invention relates generally to an implantable pacing lead and more specifically to a pacing lead having a high efficiency tissue stimulating and signal sensing porous electrode for use with a cardiac pacemaker and a method for making the porous electrode.

For a cardiac pacemaker, implant lifetime is determined by the energy delivered per pulse. The pacemaker will have a longer life if the energy delivered per pulse is maintained at a minimum. Alternatively, the energy can also be used to provide for more features in the pacemaker. The design of an implantable pacing lead which is used with the pacemaker is influenced by the optimum signal for pacing stimulation. Physiologically, a cardiac pacemaker must be capable of generating a signal with a sufficient magnitude to depolarize the excitable cells of the endocardium. The electrode size, material, surface nature, and shape; the body tissue or electrolyte conductivity; and the distance separating the electrode and the excitable tissue, combine to determine the energy required of the pacemaker. Accordingly, the main factors to be considered with regard to the design of implantable pacing lead's electrode are: the size, surface nature, material and shape; the fixation of the electrode to the tissue; and the endocardial tissue reaction.

In selecting a pacemaker, the current drain, and therefore the implant lifetime, is determined by the impedance to pacing pulses. The pacemaker lead's electrode must be capable of delivering a pacing pulse with a pulse width generally in the range of 0.01-2.0 milliseconds and 0.5 to 10.0 volts to the tissue, and to also sense and transmit a QRS signal arising in the atria and ventricles of the heart to the pacemaker circuitry. Generally, the electrode-electrolyte system impedance is higher for sensing than for pacing. Pacing leads for pacing and sensing in the atrium, which can exhibit different stimulation and depolarization parameters than the ventricle, are also required.

The electrode-endocardial tissue system impedance characteristics may be understood in terms of an interface component and a spreading resistance component. The interface component occurs within a few microns of the surface of the electrode. The spreading resistance component depends predominantly on the tissue resistivity. Generally, the former reflects the charge transfer characteristics of the electrode-tissue interface influenced mostly by the surface area and material of the electrode, and the latter reflects the overall size and shape of the electrode; the surface nature of electrode; and the resistivity of the tissue.

The current drain of a pacemaker is determined by the impedance of the pacemaker circuitry, the nature of the electrode lead resistance, and the characteristics of the electrode tip interface with the electrolyte system. For a given pacemaker circuit and electrode lead design, the current drain is well defined. Thus, the nature of the electrode-endocardial tissue interface determines the overall current requirements of the system.

As an additional design factor, the most significant frequency of the pacing pulse is on the order of 1 KHz. At this frequency, the interface impedance is small and most of the impedance to the pacing pulses is due to the bulk or spreading impedance. This is determined by the shape and size of the electrode tip and is generally inversely related to the radius of the electrode tip.

The most significant frequency components of a signal to be sensed, i.e., the ventricular QRS, are in the bandwidth of 20-100 Hz. In this region, the interface impedance of the sensed signal becomes the most significant. The interface impedance is determined in large part by the microsurface area of the electrode tip and develops within a few microns of the surface. As described herein, the microsurface area of a porous electrode tip is the wettable surface, area which includes all of the exposed and interstitial porosity surfaces of the electrode tip.

As a final design consideration, it has been determined that the pacing or stimulation threshold is a reflection of the electrical energy required for a pulse to initiate a cardiac depolarization. The stimulation threshold typically rises for a period of a few weeks after the implant of a cardiac pacemaker generally as a result of an increase in the spacing between the electrode and the excitable tissue. The increase occurs due to the development of a fibrous capsule around the electrode tip. The thickness of the fibrous capsule is generally dependent upon the mechanical characteristics of the distal end of the lead (i.e., stiff or flexible); the geometry of the electrode tip; and the microstructure of the electrode tip, such as a porous electrode surface and the electrode material itself. In this regard, the environment of the endocardium must be considered. Specifically, the constant beating of the heart can cause the electrode to pound and rub against the endocardium, causing irritation and a significant subsequent inflammatory response, which ultimately results in healing, and the development of a fibrotic tissue capsule about the electrode tip. Also, a rough surface microstructure or one with sharp protrusions for the electrode will tend to be abrasive or traumatic on the abutting heart cells, also causing irritation, which also tends to cause the development of a thicker fibrotic capsule.

In view of the above characteristics of an electrode and its implantology issues for a cardiac pacemaker, it is clear that an electrode tip with a small geometric surface area (resulting in higher pacing impedance) will have a low current drain. However, in order to enhance sensing, the same electrode tip should have a large microsurface area and be of such a material to result in a low polarization and high capacitance which, in turn, results in a low sensing impedance and improved sensing. A cardiac pacemaker electrode tip that is constructed to be porous is therefore preferred in order to best satisfy these requirements.

In a pacemaker electrode, minimal tissue reaction is desired around the tip, but firm intimate attachment of the electrode to the tissue is essential to minimize any electrode movement relative to the abutting tissue. A porous electrode tip with macro tissue entrapping structure allows rapid fibrous tissue growth into a hollow area or cavities in the electrode tip to facilitate and enhance attachment of the electrode to the heart. A reduced lead dislodgement rate is also expected as a result of such tissue ingrowth. A further aspect of importance is selection of porosity size, which must be such as to accommodate economical construction techniques, overall dimensional tolerances, and tissue response constraints.

SUMMARY OF THE INVENTION

The pacing tip electrode of the preferred embodiment of the present invention is a five square millimeter platinum-iridium (90%/10%) porous electrode with recessed areas or slots in the shape of a cross formed into the surface. The grooves allow for acute electrode stabilization tissue ingrowth as a result of naturally occurring clot formation during insertion and helps result in immediate immobilization of the electrode upon implant. A porous coating of 20–80 micron diameter spherical platinum-iridium (90%/10%) particles are deposited on the surface of the base electrode to obtain a porous macrostructure for chronic tissue ingrowth and also for extending the active surface area. Preferably, the particles are deposited in a two-step process where the first layer of particles is made up of 40 to 80 micron spheroidal particles. The second layer is made up of 20 to 40 micron spheroidal particles. The result is a clumping of the particles producing a uniformly textured surface with randomized particle attachment. Chronic tissue ingrowth into this clumped, porous macrostructure enhances the electrode stabilization. Additionally, a microstructure surface coating is applied on these particles to increase the active surface area and enhance electrical efficiency by lowering polarization and increasing electrical capacitance. The macrostructure is preferably created by sintering the platinum-iridium particles to the platinum-iridium electrode tip. The microstructure coating is preferably created by reactive sputtering of titanium nitride onto the platinum-iridium particles.

DETAILED DESCRIPTION OF THE PREFERRED EMBODIMENT

Figures 1, 7, 8:
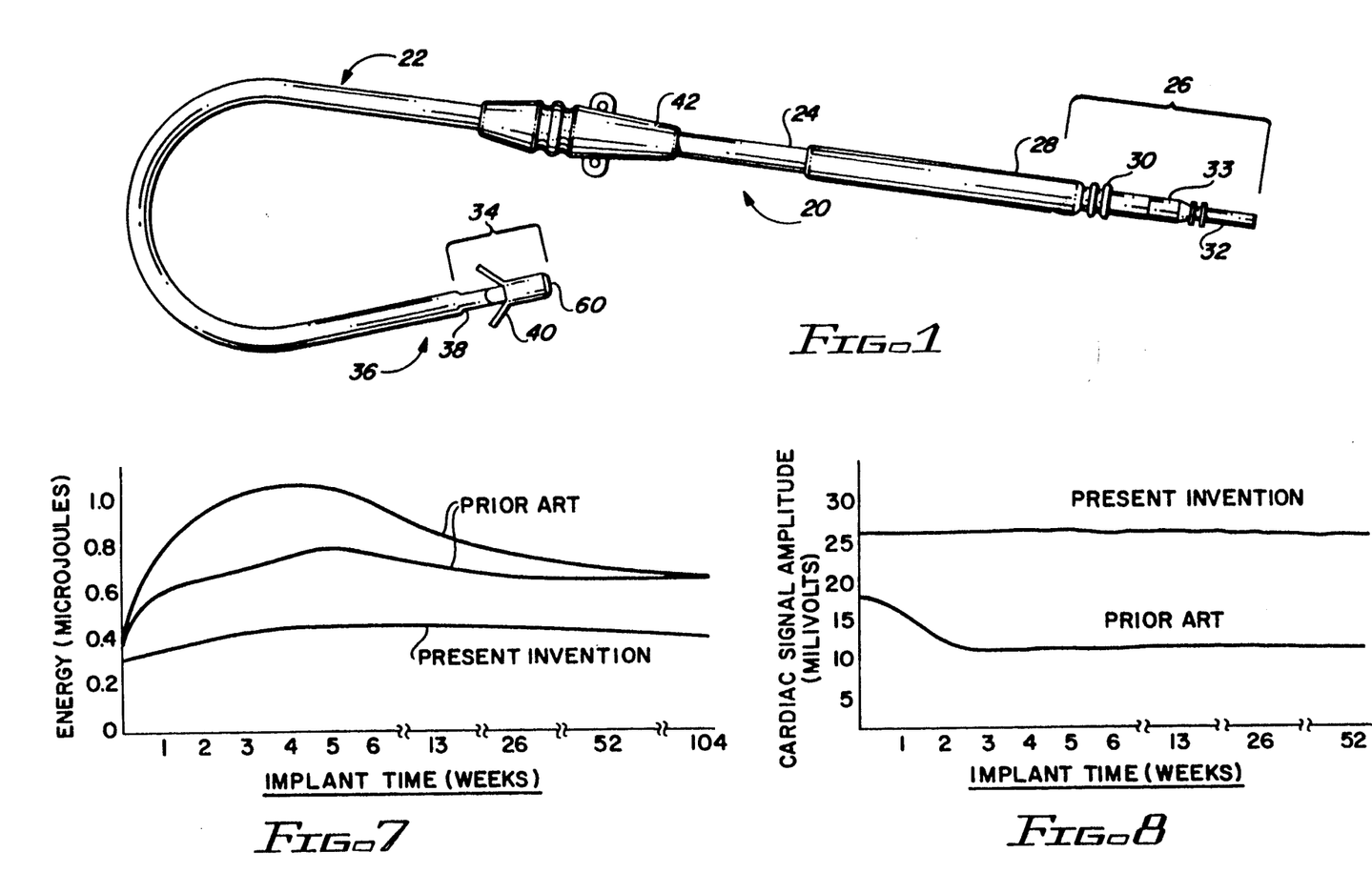
FIG. 1 shows a side plan view of a pacing lead according to the present invention.
FIG. 7 illustrates a graphical depiction of the pacing threshold performance of an electrode constructed according to the present invention.
FIG. 8 graphically depicts the improved cardiac signal sensing for the electrode of the present invention.

FIG. 1 shows a side plane view of a pacing lead 20 according to the present invention. The lead 20 is provided with an elongated lead body 22 which includes electrical conductors (not shown) covered with an insulation sheath 24. The insulation sheath is preferably fabricated of silicone rubber, polyurethane or other suitable biocompatible, biostable polymer. At a proximal end 26 of the pacing lead 20 is a connector assembly 28, which is provided with sealing rings 30 and which carries at least one electrical connector pin 32, and may also. The carry an anode terminal ring electrical connector 33. The connector assembly 28 is constructed using known techniques and is preferably fabricated of silicone rubber, polyurethane or other suitable polymer for insulating. Connector pin (or pins for bipolar or multipolar leads) 32 and connector 33 are preferably fabricated of stainless steel or other suitable conductive material.

At a distal end 34 of the pacing lead 20 is an electrode assembly 36 which is discussed in more detail below. Immediately behind the distal end of the electrode assembly 36 is a tine sheath 38 which includes a plurality of individual flexible tines 40. Tines 40 engage endocardial tissue and urge the electrode assembly 36 into contact with the endocardium, in a direction parallel to the axis of the electrode assembly 36. Tines 40 are more fully described in U.S. Pat. No. 3,902,501, issued to Citron et al., incorporated herein by reference. A fixation or lead anchoring sleeve 42, slidably mounted around lead body 22, serves to stabilize the pacing lead 20 at the site of venous insertion by means of suture ties about the sleeve and underlying fascia.

Figure 2:
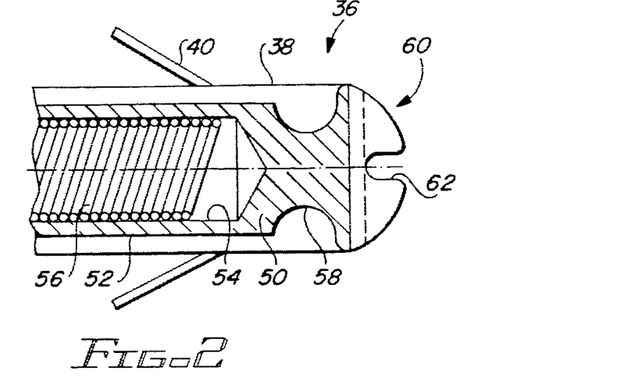
FIG. 2 shows a cross-sectional view of the distal tip of the electrode of the lead shown in FIG. 1.

The electrode assembly 36 of FIG. 1 is shown in greater cross-sectional detail in FIG. 2. As illustrated, the electrode assembly 36 includes a conductive electrode 50 as well as the tine sheath 38 and the tines 40 thereof. The conductive electrode 50 is preferably a unitary construction including, at its proximal end, a cylindrical portion 52 defining an axial bore 54. A coil-wound conductor 56 of the lead body 22 of FIG. 1 is inserted into the axial bore 54 and affixed in electrical contact thereto, for example, by mechanical crimping or welding. Proceeding toward the distal end of the conductive electrode 50, the conductive electrode 50 includes a neck area 58 having a reduced diameter from the cylinder 52 which provides a recessed area into which an interior extending ridge of the tine sheath 38 is inserted to provide positive engagement of the tine sheath 38 with the conductive electrode 50. Finally, the conductive electrode 50 terminates at an electrode distal tip 60.

As illustrated in FIG. 2, the electrode distal tip 60 has a generally mushroom shape, such that the electrode distal tip 60 has a semi-hemispherical surface which is intended to provide electrical contact with the endocardial tissue. It should be appreciated that the electrode distal tip 60 may define a number of different profiles, from semi-hemispherical to essentially planar with rounded edges. As illustrated in FIG. 2 and more specifically in FIG. 3, the electrode distal tip 60 preferably includes at least one and preferably two or more recessed areas or grooves 62. The recessed areas or grooves 62 define generally pie-shaped segments shown in FIG. 3. These pie-shaped segments of the electrode distal tip 60 will be generally defined as the plateaus 64 within the specification, although it is recognized that the plateaus may be semi-hemispherical in shape, or utilize other configurations.

Figure 3:
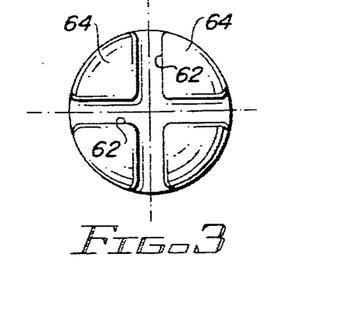
FIG. 3 shows an enlarged perspective view of the distal tip of the electrode of the lead shown in FIG. 1.

As discussed above in the background of the invention, the particular structure, i.e., the size, shape and porosity, of the electrode distal tip 60 is of particular importance to the functioning of the pacing lead 20, and the cardiac pacemaker system. The grooves 62 provide a means for capturing blood born cells during implant of the pacing lead. Specifically, the recessed areas or grooves 62 in the electrode distal tip 60 as illustrated herein, provide a capture site for blood cells and elements therein, including platelets, thrombin, red blood cells, and other elements, and the initiation of the formation of blood clotting upon insertion of the electrode assembly 36 into the vein of the recipient. As the lead body 22 of the pacing lead 20 is fed into the vein of the recipient, and the electrode assembly 36 proceeds to the heart, the platelets, thrombin, red blood cells, and other blood borne elements which are captured within the recessed areas or grooves 62 begin to form a thrombosis or blood clot. This blood clot, upon contact with the endocardial tissue, helps assist in affixing the electrode distal tip 60 to the endocardial tissue, to provide immediate stabilization of the electrode to endocardial tissue. The grooves also help to capture some amount of the soft, moldable endocardial tissue to also assist in immediately stabilizing the electrode tip.

It is anticipated that the grooves 62, while relatively shallow, will capture enough platelets, red blood cells, and other elements and endocardial tissue during the passage from the venous insertion point to the endocardium of the heart, to generally fill a majority of the recessed area. Accordingly, for a lead's electrode distal tip 60 having a diameter of between one and four millimeters, and a preferred diameter of two millimeters, the grooves 62 will have a depth in the range of between 0.1 and 0.5 millimeters and a width of between about 0.2 and 1.0 millimeters; and preferably, about 0.4 and 0.4 millimeters, respectively. Further, it is preferred that the edges of the grooves 62 be radiused in order to minimize tissue damages.

Figure 4:
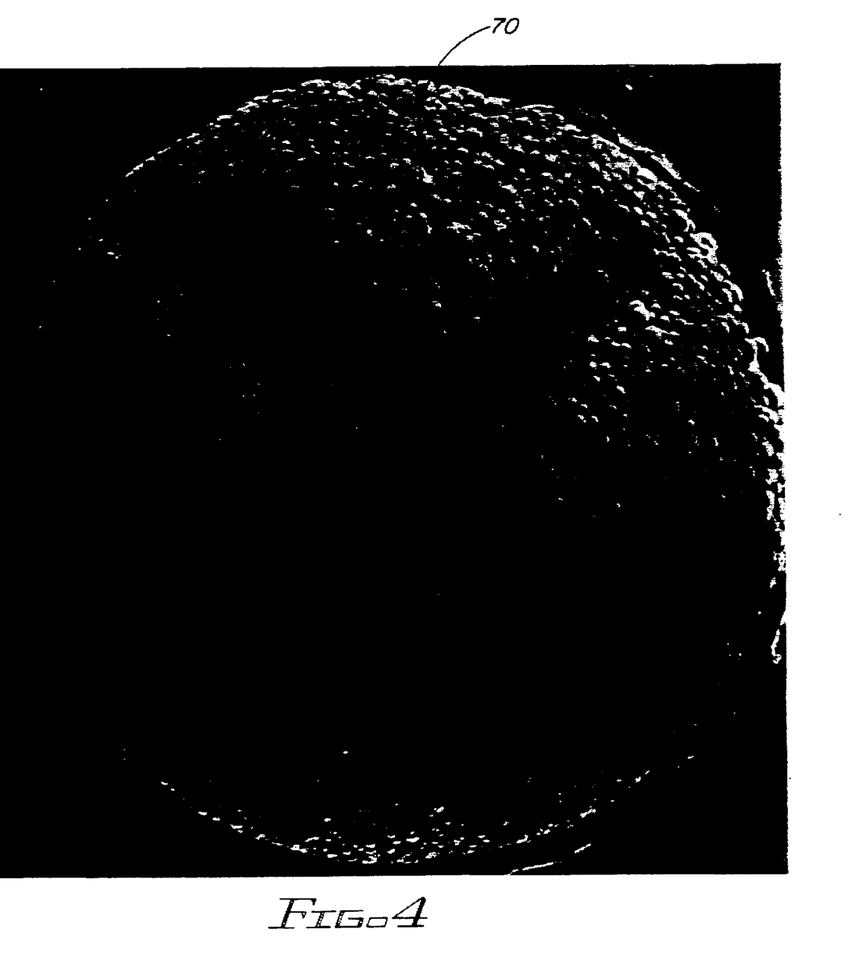
FIG. 4 shows an electron microscope photograph of the distal tip of FIG. 3, magnified by a factor of 50.
Figure 5:
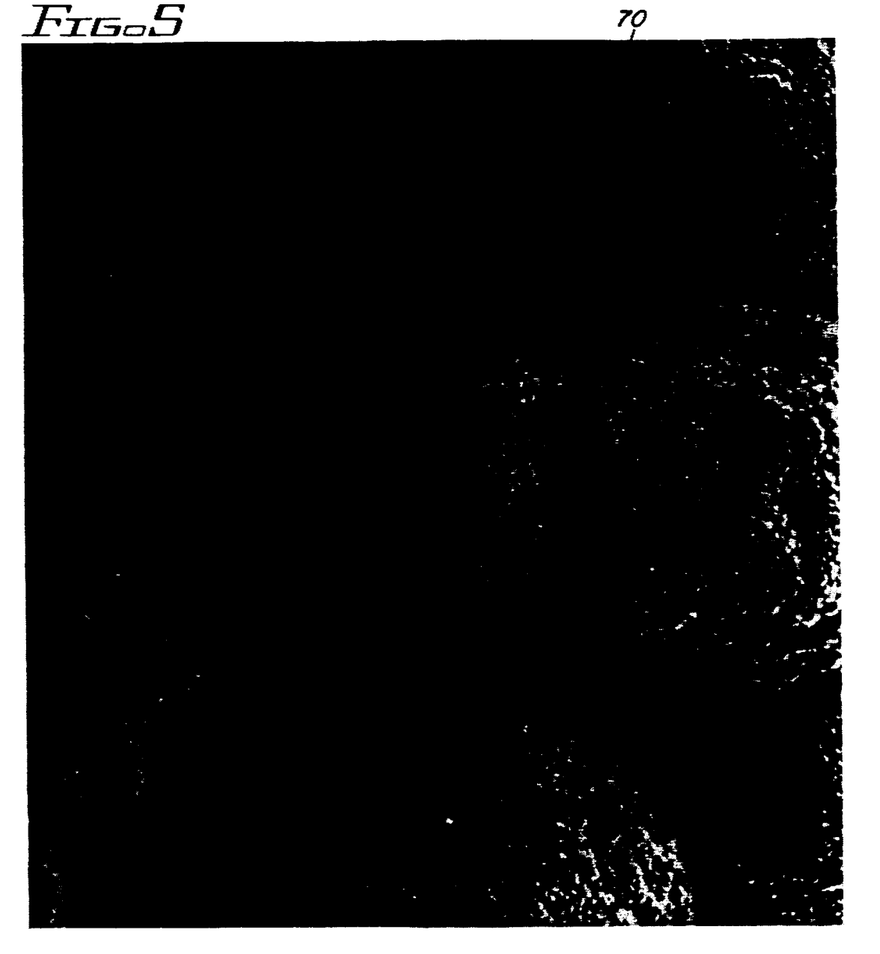
FIG. 5 shows an electron microscope photograph of the distal tip of FIG. 3, magnified by a factor of 500.

The electrode distal tip 60 is also treated to increase the porosity and active surface area, thereby enhancing the electrical efficiency by lowering the polarization and increasing capacitance. This texturizing treatment of the electrode distal tip 60 includes depositing generally spherical shaped small particles on the surface of the electrode distal tip 60, including all of the surfaces defining the recesses or grooves 62 as well as the plateaus 64. These generally spherical particles 70 are illustrated in the electron microscope photograph views shown in FIG. 4 and in FIG. 5 in greater detail.

Preferably, the conductive electrode 50 is made of a platinum-iridium composition. In the preferred embodiment, the platinum-iridium alloy has a composition of 90% platinum, 10% iridium by weight. The generally spherical particles 70 are preferably platinum/iridium (90%/100%) particles having a generally smooth surfaced spheroidal shape. It should be recognized however, that the electrode and the particles may be made of other suitable materials, such as titanium. The diameters of the spherical particles 70 should be in the range of between about 10 and 200 microns (0.01 mm to 0.20 mm), and preferably be in the range of between 20 and 80 microns (0.02 mm to 0.08 mm). Additionally, it is preferred that the spherical particles have a distribution of sizes spanning this range. Preferentially, two coatings of the spheroidal particles are applied to the base electrode. The first coating is preferred to be of particles in the range of 40-80 microns and the second coating 20-40 microns.

Upon affixation to the electrode distal tip 60, the generally spheroidal particles 70 will create a plurality of pore sites and interstitial porosity for chronic ingrowth of tissue. Preferably, by affixation of the spheroidal particles 70 having the preferred sizes and distribution of size, the interstitial porosity defined by the multiple layers of spheroidal particles 70 will have passageway dimensions which allow the passage of red blood cells (typically having a six-micron (0.006 mm) diameter) and other blood borne elements. By allowing the migration of red blood cells and other blood carried substances through the interstitial porosity, the events resulting in chronic tissue ingrowth are initiated.

The spheroidal particles 70 preferably have a generally smooth surface in order to minimize the amount of irritation of the endocardial tissue caused by the electrode distal tip 60 during the continuous beating of the heart. In addition to providing interstitial porosity for tissue ingrowth, the affixation of the spherical particles 70 also substantially increases the true surface areas of the electrode distal tip 60. Generally, by use of these spheroidal particles 70, the true surface area of the electrode distal tip 60 is increased by as much as a factor of five to twenty times.

Following affixation of the spherical particles 70 to the electrode distal tips 60, the electrode distal tip 60 and the particles 70 are treated with a surface coating means for increasing the active electrical surface area and enhancing the electrical efficiency by reducing the degree of electrochemical polarization and increasing the electrical capacitance of the electrode distal tip 60 during operation of the pacemaker system. Preferably, a nonmetallic material such as titanium nitride is used as the surface coating, as depicted in the electron microscope photograph of FIG. 6. In the electron microscope photograph of FIG. 6, a portion of the surface of the electrode distal tip 60 is enlarged by a factor of eight thousand. As may be appreciated from observing FIG. 6, the surface coating further increases the true surface area of the electrode distal tip 60 by a significant factor.

Figure 6:
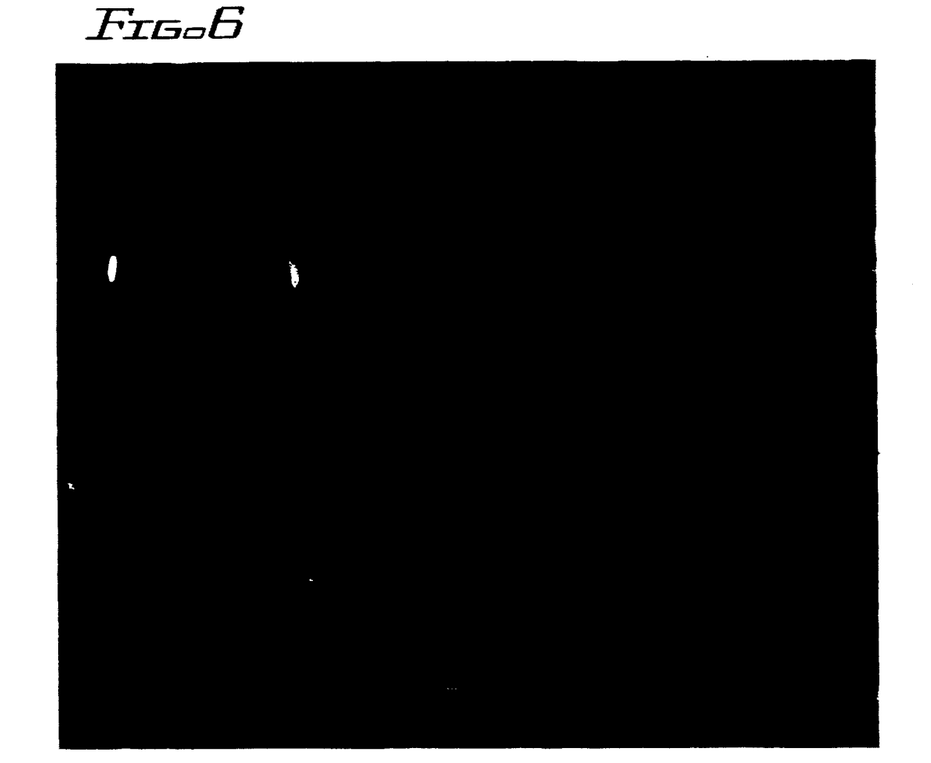
FIG. 6 shows an electron microscope photograph of the distal tip of FIG. 3, magnified by a factor 8000.

In addition to increasing the true surface area, the surface coating substantially enhances the electrical characteristics of the electrode distal tip 60. The surface coating increases the electrode's electrical capacitance and lowers the polarization developed at the electrode distal tip 60. It should also be noted that the surface coating on the spherical particles 70, while appearing to create relatively sharp edges thereon, does not result in irritation to the endocardial tissue because the relative size of the crystalline structure of the surface coating is substantially smaller than the heart's cells, the other cardiovascular tissue, and the blood elements which the coating will contact (i.e., red blood cells having an approximate diameter of six microns).

The surface coating is deposited in a manner such that the thicknesses of the surface coating attached to the spherical particles 70 is in a range of between one to thirty microns. While titanium nitride is the preferred surface coating material, other suitable nonmetallic coating materials, such as, for example, carbon, iridium oxide, and titanium oxide; and platinum oxide may also be applied as the surface coating of the electrode distal tip 60 following affixation of the spherical particles 70.

FIG. 7 is a graph depicting the generalized pacing threshold performance of an electrode constructed according to the present invention. In FIG. 7, the pacing threshold energy in microjoules is depicted on the Y-axis as a function of time, in weeks, along the X-axis, for two exemplary lead designs of the prior art and the lead 20 according to the present invention. In the graph, the average energy threshold is based upon voltage thresholds at various pulse duration and assumes pacing impedance remains generally constant. As depicted, the increase in the average energy requirement within the four to six weeks following implant is substantial for the pacing leads of the prior art. By comparison, the lead 20 of the present invention exhibits virtually no threshold increase, and remains relatively level at a lower average energy than either of the prior art leads. As may be appreciated, this will result in an increased threshold safety margin and/or a substantial increase in the useful life of the pacemaker system, given a fixed battery capacity since the required energy to stimulate the heart is low.

FIG. 8 graphically depicts the improved cardiac signal sensing capability of the electrode design of the present invention. In FIG. 8 the cardiac signal amplitude in millivolts is depicted on the Y-axis as a function of time (in weeks) on the X-axis, for the lead of the present invention and a lead according to the prior art. As depicted, the lead of the present invention maintains a relatively uniform high level for the cardiac signal amplitude, as compared to the prior lead which has both a lower initial level and a reduction over the course of the first two to three weeks. The primary difference reduced as a result of the significantly reduced polarization of the lead of the present invention, as discussed in greater detail below.

Figure 9:
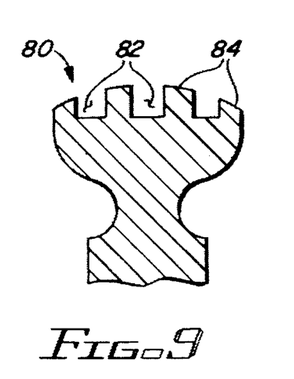
FIG. 9 is a cross-sectional view of an alternative configuration for the distal tip of FIG. 1.
Figure 10:
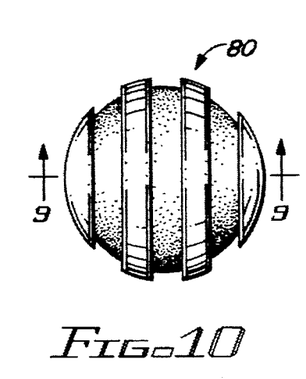
FIG. 10 is a plan view of the alternative tip configuration of FIG. 9.

FIGS. 9 and 10 show a cross-sectional view and a top view of an alternative embodiment of an electrode distal tip electrode so for the electrode assembly 36 of FIG. 1. In FIGS. 9, 10, the electrode distal tip 80 includes a plurality of generally parallel grooves 82 defining therebetween generally parallel strip plateau sections 84. In the embodiment shown in FIG. 9, three grooves 82 are illustrated; however, it should be understood that a limited number of additional grooves may be incorporated. The number of the grooves 82 is limited by the size of the grooves appropriate for the capture of platelets, red blood cells, and other blood elements and tissue as described above, and the diameter of the electrode distal tip 80. In the preferred configuration, the diameter of the electrode distal tip 80 will be in the range of between one to four millimeters. Preferably, the diameter of the electrode distal tip 80 is approximately two millimeters.

Figure 11:
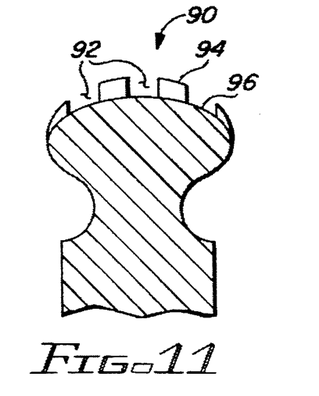
FIG. 11 is a cross-sectional view of a second alternative configuration for the distal tip of FIG. 1.
Figure 12:
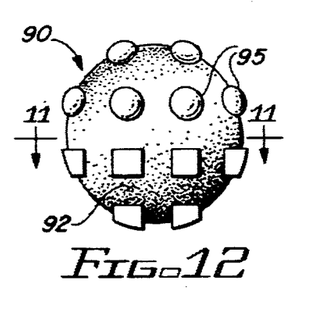
FIG. 12 is a plan view of the alternative tip configuration of FIG. 11.

FIGS. 11 and 12 show a cross-sectional view and a top plan view respectively of a second alternative embodiment of an electrode distal tip 90 for the electrode assembly 36 of FIG. 1. The embodiment of FIGS. 11 and 12 includes a plurality of intersecting grooves 92 which define therebetween generally square shaped plateaus 94. Alternatively the plateaus may be round in shape as shown by round plateau 95. As above, the grooves 92 are dimensioned so as to allow capture of platelets, red blood cells, and other blood elements during insertion of the lead 20 into the patient. In addition, as illustrated in FIG. 11, the grooves 92 are cut into the electrode distal tip 90 such that a base 96 of the grooves, when viewed in cross-section, defines a semi-hemispherical inner surface. Thus, in FIGS. 11 and 12, both the surfaces of the plateaus 94 and the base 96 of the grooves 92 define semi-hemispherical surfaces. This semi-hemispherical base surface configuration can also be incorporated into the designs illustrated in FIGS. 2 and 3, as well as in the design of FIGS. 9 and 10.

Figure 13:
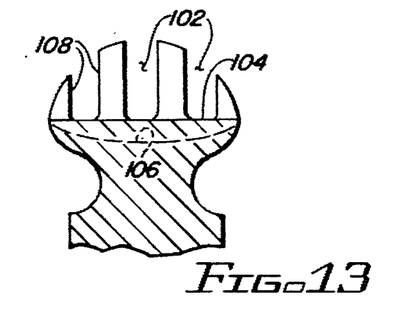
FIG. 13 is a cross-sectional view of an alternative configuration for the distal tip of FIGS. 2-3 or 9-12.

An additional alternative design configuration which may be incorporated into any of the three embodiments illustrated in FIGS. 2 and 3, 9 and 10, or 11 and 12, is illustrated in FIG. 13. In FIG. 13, the base of the grooves 102 is illustrated as either having a flat surface 104 or a concaved inner surface 106. Thus, in any of the electrode distal tip configurations of the present invention, it is contemplated that the base of the groove or grooves may define a concave base surface, a flat base surface or a semi-hemispherical base surface profile.

Additionally, while it has been illustrated in the figures that the walls 108 (FIG. 13) defining the grooves of the embodiments are illustrated as having generally flat surfaces which parallel the axis of the distal tip, it may be appreciated that the walls of the grooves may be generally angled with respect to the axis of the distal tip. In addition, the corners at the base and the peaks of the grooves for any of 30 the above described embodiments may be radiused to a radius of curvature of between about 0.001 mm and 0.5 mm, as opposed to having sharp edges. The grooves of any of the above embodiments may be formed by any of the methods selected from the group including stamping, milling, molding and electrochemical machining. The generally spherical particles 70 which are applied to the surfaces of the electrode distal tip 60 as discussed above with respect to FIG. 1 are also applied to the alternative embodiments of FIGS. 9 through 13, as is the titanium nitride or alternative surface coating treatment. The spherical particles 70 are preferably attached to the surfaces of the electrode distal tip by a process selected from the group of processes including sintering, laser fusion or welding, injection and molding casting. An example of one such attachment process is powder sintering, wherein a fractional percentage of the spherical particles are affixed in each of two to five successive steps.

Finally, the surface coating of titanium nitride or alternative material, is applied to the spherical particles 70 of the electrode distal tips 60 or any of the alternative embodiments of FIGS. 9 through 13 by a process selected from the group including sintering in an appropriate environment, vapor deposition, electroplating and sputtering.

Figure 14:
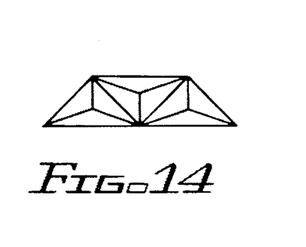
FIGS. 14 and 15 schematically depict top and side views respectively of the microporous surface structure.
Figure 15:
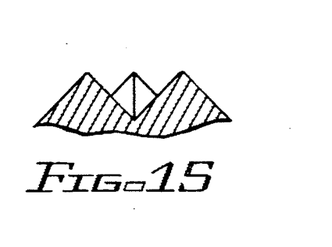

The surface coating is illustrated in FIGS. 14 and 15 which schematically depict top and side views respectively of the microporous surface structure. FIG. 14 illustrates the generally pyramid-like shape of the microporous coating. In FIG. 15, a side or profile view of the microporous surface coating illustrates the triangular peaks of the coating, and more importantly the areas between the peaks of the coating which provides high surface porosity. With the foregoing construction, incorporating the microporous surface coating, the surface porosity or microporosity is in excess of fifty percent (50%), and preferably in the range of between sixty-five percent (65%) and seventy percent (70%).

A pacing lead having an electrode tip configured in accordance with the foregoing detailed description exhibits superior pacing performance. The primary reason for the superior performance is the reduction in polarization proximate the electrode tip. The "polarization voltage" for a pacing lead is herein defined to be the voltage differential developed between the leading edge and the trailing edge of a reference electrical impulse. The reference electrical impulse is a 10 mA (milliampere), one millisecond, square wave, constant current pulse from a pulse generator. The polarization voltage (Pv) for a particular pacing lead is determined by subtracting the leading edge voltage (V1) from the trailing edge voltage (V2) of the reference electrical impulse (Pv=(V2−V1). During measurement of the polarization voltage, the electrode is immersed in a 0.15 molar sodium chloride (NaCl) solution, at a pH of 7, and temperature of 37° C.

As may be appreciated by those skilled in the art, the polarization voltage measured according to the above test will be influenced substantially by the size, shape, material, and surface nature of the electrode distal tip for a given pacing lead. Thus, for an electrode distal tip having a particular profile, and made of a particular material having a particular surface nature, the polarization voltages will be different for a 3 mm$^2$ tip and a 5 mm$^2$ tip. Conversely, two pacing leads having 5 mm$^2$ electrode tips will have characterizing polarization voltages which will depend on their particular profile, construction, material and surface nature. Generally the pacing lead electrode which has a lower polarization voltage for any given electrode design, or more simply the circumferential area, (cross-sectional area for a non-round tip) will be the more desirable pacing lead.

Accordingly, to further characterize pacing lead electrodes and more particularly the pacing lead of the present invention, a "polarization index" (PI) is herein defined. The polarization index is the polarization voltage Pv divided by the circumferential area CA (or cross-sectional area) of the electrode at its widest diameter. Thus, for a semi-spherical electrode having a diameter "d," the circumferential area CA is equal to $\pi(d/2)^2$, and the polarization index is given by the following formula:

$$PI = (V2-V1)/\pi(d/2)^2 \text{ or } PI = Pv/CA$$

The pacing leads of the present invention as disclosed in detail above have a polarization index PI which is less than 100 mV/mm$^2$. More particularly, in the preferred embodiments, the pacing leads of the present invention have a polarization index PI which is less than 50 mV/mm$^2$. A pacing lead having an electrode tip which combines a surface morphology allowing tissue ingrowth and very low polarization index levels is highly desirable in the field of implantable cardiac pacing leads.

It should be evident from the foregoing description that the present invention provides many advantages over pacing leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable pacing lead for use with a cardiac pacemaker comprising:
    an electrical conductor having a proximal end and a distal end;
    an insulative sheath covering said conductor;
    an electrical connector coupled to said proximal end of said conductor; and
    an electrode coupled to said distal end of said conductor, said electrode having an electrode tip geometry macrostructure defining at least two plateau sections separated by at least one recessed groove section, said plateau sections and said recessed groove section including surfaces having affixed thereto at least one layer of generally spheroidal conductive particles, said spheroidal particles coated with a layer of nonmetallic material selected from the group consisting of titanium nitride, iridium oxide, titanium oxide, platinum oxide, palladium oxide and activated forms of carbon, said layer of material having a surface morphology which results in a porosity of greater than about fifty percent.

2. The pacing lead of claim 1, wherein said generally spherical conductive particles have diameters ranging from about 10–200 microns, said particles configured in at least one layer on said electrode surfaces to provide interstitial porosity for tissue ingrowth.

3. The pacing lead of claim 2, wherein said electrode includes two recessed areas configured to intersect one another defining a cross shape.

4. The pacing lead of claim 2, wherein said electrode includes at least two sets of multiple, parallel aligned, recessed areas, configured to have said multiple aligned recessed areas of said sets intersecting one another.

5. The pacing lead of claim 1, wherein said spheroidal conductive particles are formed of a material selected from the group consisting of platinum, titanium, palladium, platinum-iridium, and carbon, said particles configured in at least one layer on said electrode surfaces to provide interstitial porosity for tissue ingrowth.

6. The pacing lead of claim 5, wherein a majority of said interstitial porosity areas between said particles have a plurality of passage diameters greater than six microns to allow passage of blood cells 7. The pacing lead of claim 5, wherein said electrode includes at least two parallel aligned recessed areas defining at least three generally aligned plateau areas, and wherein the corners of said plateau areas each define an angle of at least sixty degrees.

8. The pacing lead of claim 5, wherein said at least one recessed groove section has a profile defined by a depth of between 0.1 and 1.0 millimeters, a width of between about 0.2 and 1.5 millimeters, and each edge of said groove is radiused with a radius of curvature of between about 0.001 and 0.5 millimeters.

9. An implantable pacing lead for use with a cardiac pacemaker comprising:
    an electrical conductor having a proximal end and a distal end;
    an insulative sheath covering said conductor;
    an electrical connector affixed to said proximal end of said conductor; and
    an electrode assembly affixed to said distal end of said conductor, said electrode assembly including a porous electrode distal tip having a polarization index PI which is less than 100 mV/mm$^2$.

10. The implantable pacing lead of claim 9, wherein said electrode distal tip further comprises:
    at least one recessed area for capturing blood cells during insertion of said electrode assembly into a human recipient, and for promoting clot formation and endocardial tissue capture thereof to aid fixation of said electrode distal tip to endocardial tissue;

means for providing interstitial porosity and for increasing surface area of said electrode distal tip; and coating means for enhancing the electrical characteristics of said electrode distal tip, for increasing the electrical capacitance, and for reducing electrochemical polarization at the electrode-endocardial tissue interface during pacing use.

11. The implantable pacing lead of claim 10, wherein said at least one recessed area traverses said electrode distal tip, said at least one recessed area having a generally U-shaped profile defined by generally vertical walls and a base, said base having a transverse profile shape selected from the group consisting of semi-hemispherical, flat and concave.

12. The implantable pacing lead of claim 11, wherein said means for providing interstitial porosity and increasing surface area comprises:

a plurality of generally smooth surfaced spheroidal particles affixed to the surfaces of said electrode distal tip including said walls and base of said at least one recessed area.

13. The implantable pacing lead of claim 12, wherein said coating means comprises:

a surface coating applied to the surfaces of said distal tip electrode and said spheroidal particles thereon, said surface coating comprising a microscopically thin layer of a nonmetallic material selected from the group consisting of titanium nitride, titanium oxide, carbon, iridium oxide, and platinum oxide, said surface coating applied by a process selected from the group consisting of sintering, vapor deposition, electroplating and sputtering.

14. The implantable lead of claim 13, wherein said electrode distal tip further comprises:

at least two plateau areas separated by said at least one recessed area, said plateau areas having a generally semi-hemispherical profile.

15. The implantable pacing lead of claim 13, wherein said electrode distal tip includes two recessed areas configured to intersect one another, defining a cross-like shape.

16. The implantable pacing lead of claim 13, wherein said electrode distal tip includes at least two parallel aligned recessed areas defining at least three generally aligned plateau areas.

17. The implantable pacing lead of claim 13, wherein said electrode distal tip includes at least two sets of multiple, parallel aligned recessed areas, configured to have said multiple aligned recessed areas of said sets intersecting one another.

18. The implantable pacing lead of claim 13, wherein said at least one recessed area has a depth of between 0.1 and 1.0 millimeters and a width of between about 0.2 and 1.5 millimeters.

19. The implantable pacing lead of claim 13, wherein said plurality of generally smooth surfaced spheroidal particles have diameters distributed in the range of between about 10-200 microns, said particles formed of a material selected from the group consisting of platinum, platinum-iridium, titanium, palladium and carbon.

20. The implantable pacing lead of claim 13, wherein said electrode assembly has an electrode distal tip having a polarization index PI which is less than 50 mV/mm$^2$.

21. A method of forming an implantable pacing lead for use with a cardiac pacemaker comprising:

providing an electrical conductor having a proximal end and a distal end;

covering said conductor in an insulative sheath;

coupling an electrical connector to said proximal end of said conductor;

forming an electrode having an electrode tip geometry macrostructure defining at least two plateau sections separated by at least one recessed groove section;

affixing to said plateau sections and said recessed groove section a plurality of generally spherical conductive particles;

coating said particles with a layer of nonmetallic material selected from the group consisting of titanium nitride, palladium, platinum oxide, iridium oxide, and activated carbon; and coupling said electrode to said distal end of said conductor.

22. The method of forming an implantable pacing lead of claim 21, wherein said coating of said particles is performed by a process selected from the group consisting of vapor deposition sintering, electroplating and electrode sputtering to a thickness of between 20-30 microns.

23. The method of forming the implantable pacing lead of claim 21, wherein said generally spherical conductive particles are affixed to said electrode distal tip by a process selected from the group consisting of powder sintering, laser fusion, welding, injection molding, and casting.

24. The method of claim 23, wherein said generally spheroidal conductive particles are affixed by one of said processes in a series of successive steps in which a portion of the particles are affixed by said process in each of said successive steps.

* * * * *